(12) United States Patent
Mitta et al.

(10) Patent No.: US 7,531,509 B2
(45) Date of Patent: May 12, 2009

(54) PAPILLOSIN ANTIMICROBIAL PEPTIDE, A GENE CODING SAID PEPTIDE, A VECTOR, A TRANSFORMED ORGANISM AND A COMPOUND CONTAINING SAID ORGANISM

(75) Inventors: Guillaume Mitta, Baho (FR); Richard Galinier, Perpignan (FR); Bernard Banaigs, Canet-en-Roussillon (FR); Eric Lasserre, Villeneuve-de-la Raho (FR)

(73) Assignees: Centre National de la Recherche Scientifique—CNRS (FR); Universite de Perpignan (FR)

( * ) Notice: Subject to any disclaimer, the term of this patent is extended or adjusted under 35 U.S.C. 154(b) by 126 days.

(21) Appl. No.: 10/547,562

(22) PCT Filed: Mar. 5, 2004

(86) PCT No.: PCT/FR2004/000535

§ 371 (c)(1),
(2), (4) Date: Dec. 28, 2005

(87) PCT Pub. No.: WO2004/081214

PCT Pub. Date: Sep. 23, 2004

(65) Prior Publication Data

US 2006/0205640 A1 Sep. 14, 2006

(30) Foreign Application Priority Data

Mar. 5, 2003 (FR) .................................. 03 02714

(51) Int. Cl.
*A61K 38/00* (2006.01)
*C07K 5/00* (2006.01)
*C12N 15/00* (2006.01)
*C07H 19/00* (2006.01)
*C07H 21/02* (2006.01)
*A01N 37/18* (2006.01)

(52) U.S. Cl. .................. 514/12; 530/310; 530/324; 530/300; 435/320.1; 536/22.1; 536/23.1; 536/23.5; 514/2; 514/21

(58) Field of Classification Search ........................ None
See application file for complete search history.

(56) References Cited

FOREIGN PATENT DOCUMENTS

WO   WO 98/20028 A2   5/1998
WO   WO 98/38309 A1   9/1998

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Potrykus, Gene transfer to cereals: an assessment, Biotechnology, 1990, 8(6):535-542.*
Brand et al. (J. Biol. Chem., 277(51): pp. 49332-49340, 2002).*
C.V.F. Batista et al., *Antimicrobial peptides from the Brazilian frog Phyllomedusa distincta*, Peptides, United States, vol. 20, No. 6, 1999, pp. 679-686.
In Hee Lee et al., *Dicynthaurin: an antimicrobial peptide from hemocytes of the solitary tunicate, Halocynthia aurantium*, Biochimica et Biophysica Acta, Elsevier Science B.V., the Netherlands, vol. 1527, No. 3, Aug. 15, 2001, pp. 141-148.
A. Tossi et al., *Molecular Diversity in Gene-Encoded, Cationic Antimicrobial Polypeptides*, Current Pharmaceutical Design, the Netherlands, vol. 8, No. 9, 2002, pp. 743-761.
Woong Sik Jang et al., *Halocidin: a new antimicrobial peptide from hemocytes of the solitary tunicate, Halocynthia aurantium*, FEBS Letters, Elsevier Science B.V., the Netherlands, vol. 521, No. 1-3, Jun. 19, 2002, pp. 81-86.

* cited by examiner

*Primary Examiner*—Rebecca E Prouty
*Assistant Examiner*—Jae W Lee
(74) *Attorney, Agent, or Firm*—DLA Piper LLP (US)

(57) ABSTRACT

An antimicrobial peptide isolated from an extract from a marine invertebrate, whose amino acid sequence is as follows:
GFWKKVGSAAWGGVKAAAKGAAVGGLNALAK-HIQ (SEQ ID No. 1), its derivatives, its fragments and a polypeptide, as well as transformed host organisms capable of producing the peptide such as microorganisms, animal cells, digital cells and plants, and an antimicrobial composition containing the peptide.

13 Claims, No Drawings

SEQUENCE LISTING

<160> NUMBER OF SEQ ID NOS: 1

<210> SEQ ID NO 1
<211> LENGTH: 34
<212> TYPE: PRT
<213> ORGANISM: Halocynthia papillosa -continued

```
<400> SEQUENCE: 1

Gly Phe Trp Lys Lys Val Gly Ser Ala Ala Trp Gly Gly Val Lys Ala
 1               5                  10                  15

Ala Ala Lys Gly Ala Ala Val Gly Gly Leu Asn Ala Leu Ala Lys His
            20                  25                  30

Ile Gln
```

PAPILLOSIN ANTIMICROBIAL PEPTIDE, A GENE CODING SAID PEPTIDE, A VECTOR, A TRANSFORMED ORGANISM AND A COMPOUND CONTAINING SAID ORGANISM

RELATED APPLICATIONS

This is a §371 of International Application No. PCT/FR2004/000535, with an international filing date of Mar. 5, 2004 (WO 2004/081214, published Sep. 23, 2004), which is based on French Patent Application No. 03/-2714, filed Mar. 5, 2003.

FIELD OF THE INVENTION

This invention relates to a novel antimicrobial peptide called "papillosin" in the following, identified and purified from an extract from a marine invertebrate.

BACKGROUND

Numerous diseases (tuberculosis, pneumonia, urinary pathologies, etc.) that have been well under control since the advent of antibiotics now constitute reemerging pathologies, often with a fatal prognosis, as a consequence of the impotence of classic antibiotics.

In fact, tuberculosis, formerly an implacable scourge (caused by the bacillus Mycobacterium tuberculosis), had regressed in the last forty years in the industrialized countries due to the amelioration of social conditions and to the application of an efficacious antibiotic treatment. It reappeared in a more virulent form in the middle of the 1980's in numerous countries, including France and the United States. The "new" forms of the bacillus are resistant to classic tuberculosis drugs (streptomycin, isoniazid, rifampicin) as well as to other antibiotics, which are hardly efficacious.

Likewise, the infections called "nosocomial" frequently contracted in a hospital environment are most often very difficult to bring under control on account of their resistance to available antibiotics. 20 to 25% of pneumococci isolated in a hospital environment turned out to be resistant to the antibiotics of the family of macrolides and 20 to 40% of the *Staphylococcus aurei* isolated in hospitals in the USA are resistant to methicillin.

The existence and constant appearance of bacteria that are more and more resistant to antibiotics is putting a significant demand on the pharmaceutical industry and making it absolutely necessary to discover new families of antibiotics.

The marine biotope is considered the richest of the various habitats of the globes but also is the least well known by scientists. It is also the prebiotic cradle of our planet (3 billion years of evolution). As a consequence. this provides a diversity of species, systems of organization, forms and adaptive solutions. This biodiversity is a source of a formidable chemodiversity, a potential source of new natural compounds. Research has already led to the discovery of substances that are remarkable on account of their structures as well as their biological activities. Several thousands of substances have been indexed. More than 150 publications describing new secondary metabolites have appeared each year for more than 10 years. Some of these metabolites constitute subject matter of clinical trials or have already been commercialized. Other compounds such as toxins from marine microorganisms (ciquatoxin, brevetoxin, saxitoxin or tetrodotoxin) are tools of choice in neurophysiology and in particular in the study of ionic channels.

At the present time, more than one half of molecules with a marine origin capable of being used in the health field are intended for the treatment of cancers. In twenty-five years, from 1970 to 1995, more than 130 marine substances were patented in the world for their therapeutic properties.

Curiously, the area of antibiotics has been somewhat forgotten. The investigation of new antibiotic peptides in marine invertebrates has only been very recently approached. Antimicrobial peptides are molecules whose target is the bacterial membrane. Consequently, to acquire a resistance to these type of molecules, the microorganisms must change the composition and organization of their membrane lipids. This solution, which is costly from an evolutionary viewpoint, explains why the resistance of microorganisms to this type of antibiotics is only rarely referenced.

SUMMARY OF THE INVENTION

This invention relates to an isolated peptide having an amino acid sequence GFWKKVGSAAWGGVKAAAK-GAAVGGLNALAKHIQ (SEQ ID No. 1), its derivatives and its fragments containing at least 7 amino acids.

This invention also relates to an antimicrobial composition including as an active agent the peptide having an amino acid sequence GFWKKVGSAAWGGVKAAAKGAAVG-GLNALAKHIO (SEQ ID No. 1), its derivatives and its fragments containing at least 7 amino acids and a pharmaceutically acceptable vehicle.

This invention further relates to a method for preventing and/or treating a microbial infection including administering a therapeutically effective amount of the peptide having an amino acid sequence GFWKKVGSAAWGGVKAAAK-GAAVGGLNALAKHIQ (SEQ ID No. 1), its derivatives and its fragments containing at least 7 amino acids.

DETAILED DESCRIPTION

We have now purified a novel antibiotic peptide, called "papillosin," taking into account the fact that it does not have a primary structural homology relative to other molecules described in the literature and that it was purified from a type of tunicate (urochorda), the solitary sea squirt *Halocynthia papillosa* in which this type of molecule has never been researched. The antimicrobial activity of papillosin was evaluated in the laboratory: It is a bacteriolytic molecule that is essentially active against gram-positive and gram-negative bacteria. This molecule is particularly interesting on account of its particular mode of action. In fact, it does not permit the induction of resistance on the part of bacterial targets.

In the peptidic sequences cited below, the amino acids are represented by their one-letter codes but they can also be represented by their three-letter code in accordance with the following nomenclature:

| A | Ala | alanine |
|---|-----|---------|
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagines |
| P | Pro | praline |

-continued

| Q | Gln | glutamine |
| R | Arg | arginine |
| S | Ser | serine |
| T | Thr | threonine |
| V | Val | valine |
| W | Trp | tryptophane |
| Y | Tyr | tyrosine |

This invention, therefore, relates to an isolated peptide of 34 amino acids whose amino acid sequence is as follows:

GFWKKVGSAAWGGVKAAAKGAAVG-
GLNALAKHIQ (SEQ ID No. 1), its derivatives and its fragments.

"Derivatives" of the peptide in accordance with the invention that can be cited are the peptides that have a post-translation modification and/or a chemical modification, in particular a glycosylation, an amidation, an acylation, an acetylation, a methylation, as well as the peptides carrying a protective group. "Protective group" denotes any group that permits degradation of the peptide of the invention to be avoided.

The derivatives of the peptide can also be those of which one or several amino acids are enantiomers, diastereoisomers, natural amino acids with D conformation, rare amino acids, especially hydroxyproline, hydroxylysine, allohydroxylysine, 6-N methylysine, N-ethylglycine, N-methylglycine, N-ethylasparagine, allo-isoleucine, N-methylisoleucine, N-methylvaline, pyroglutamine, aminobutyric acid and synthetic amino acids, especially orinithine, norleucine, norvaline, cyclohexyl-alanine and the omega amino acids. The invention also covers the retropeptides and the retroinversopeptides as well as the peptides whose lateral chain of one or several amino acids is substituted by groups that do not modify the antimicrobial activity of the peptide of the invention.

"Derivatives" of the peptide of the invention also denote peptides with 70%, 75%, 80%, 85%, 90% and/or 95% homology with the peptide of sequence SEQ ID No. 1.

"Fragments" of the peptide of the invention denote fragments of at least 7 amino acids that have antibacterial activity. The antimicrobial activity of the derivatives and fragments of the peptide are demonstrated by in vitro tests described below in the examples.

The invention also relates to an isolated polypeptide comprising the peptide of the invention. The invention envisages in particular a polypeptide comprising the peptide of which the one and/or the other end(s) of the peptide comprise(s) one or several amino acids necessary for its expression and/or its targeting in a host organism.

The peptide, its derivatives and its fragments, just as the polypeptides of the invention, can be synthesized chemically in accordance with known techniques.

The invention also relates to an isolated polynucleotide that codes the peptide or a polypeptide of the invention. The term "polynucleotide" denotes a nucleic sequence of the DNA or RNA type, preferably DNA, especially double-stranded. Those skilled in the art who know the genetic code and amino acid sequence of the peptide of the invention are able to isolate a polynucleotide coding the peptide of the invention by targeting banks of nucleic acid by using one or several oligonucleotides deduced from the amino acid sequence of the peptide of the invention. Those skilled in the art also have at their disposal computer software capable of supplying, from an amino acid sequence, the corresponding nucleotide sequence (protein in reverse code).

The invention also relates to isolated polynucleotides that comprise modifications at the level of one or several nucleotides resulting from the degeneration of the genetic code and that code for one and the same amino acid sequence of the peptide of the invention.

The invention also relates to isolated polynucleotides coding for the peptide or a polypeptide of the invention and capable of hybridizing under conditions stringent for this peptide or these polypeptides. The term "stringent conditions" denotes the conditions taught by Sambrook et al., (Molecular Cloning, 1989, C. Noland ed., New York, Cold Spring Harbor Laboratory Press).

The invention also relates to the complementary nucleotide sequences of the isolated polynucleotides defined above as well as the corresponding RNAs.

The invention also relates to a cloning and/or expression vector containing a polynucleotide in accordance with the invention for transforming a host organism and expressing in the latter the peptide or a polypeptide of the invention. The cloning and/or expression vector can advantageously contain, aside from the polynucleotide coding a peptide or a polypeptide of the invention, at least one element selected from the group consisting of promoters, inducible promoters and terminator elements.

This vector preferably comprises a promoter, a polynucleotide coding the peptide or a polypeptide of the invention and a terminator element, connected to each other in an operational manner. The term "connected to each other in an operational manner" denotes elements connected to each other in such a manner that the functioning of one of the elements is affected by that of another one. For example, a promoter is connected in an operational manner to a coding sequence when it is capable of affecting the expression of the latter. The regulating elements of the transcription, the-translation and the-maturation of the peptides that the vector can comprise are known and may be selected as a function of the host organism in which the expression or the cloning is to be realized.

The vector of the invention is advantageously selected from a plasmid, a cosmid, a bacteriophage and a virus, in particular, a baculovirus. The peptide of the invention is preferably a vector with autonomous replication comprising elements permitting its maintenance and replication in the host organism as an origin of replication.

Furthermore, the vector can comprise elements permitting its selection in the host organism such as, e.g., a gene resistant to an antibiotic or a selection gene that assures a complementation with the respective gene deleted at the level of the genome of the host organism. Such cloning and/or expression vectors are well known and widely described in the literature.

The invention also relates to a host organism that is transformed with the aide of a vector in accordance with the invention. The term "host organism" denotes any mono- or pluricellular, lesser or greater organism in which a polynucleotide of the invention is introduced for the production of a peptide or of a polypeptide of the invention. Those skilled in the art know different methods for introducing a polynucleotide efficaciously into a host organism such that the peptide or polypeptide coded by this polynucleotide is produced in the host organism. By way of example and in a non-exhaustive manners this method can be an electroporation, a lipofection, a biological transformation of a plant using *Agrobacterium tumefasciens*, etc.

According to one aspect, the host organism is a microorganism such as a yeast, bacteria or fungus. The transformation of such microorganisms permits production of the peptide of the invention on a semi-industrial or industrial scale.

Those skilled in the art know such microorganisms and how to transform them without undue effort.

According to another aspect, the host organism is an animal cell such as a mammalian cell.

According to yet another aspect, the host organism is a cell of a vegetable or of a plant. The term "plant cell" denotes any cell that stems from a plant and can constitute non-differentiated tissues such as calluses, differentiated tissues such as embryos, parts of plants, plants or seeds. The term "plant" denotes any differentiated multicellular organism capable of photosynthesis, in particular, monocotyledons or dicotyledons and, more particularly, cultivated plants intended or not for animal or human food.

Consequently, the host organism of the invention is selected from microorganisms, animal cells, vegetal cells and plants.

The peptide of the invention is also useful for conferring on plants a character of resistance to microbial diseases. The invention therefore also relates to a vegetal cell resistant to microbial diseases comprising a polynucleotide of the invention. The invention also relates to a plant comprising at least one vegetal cell resistant to microbial diseases as defined above.

Finally, the invention intends to profit from the antimicrobial properties of the peptide of the invention for preventing and/or treating microbial infections in humans, animals and in plants. The term "antimicrobial properties" denotes antibacterial properties as well as antifungal properties. The invention thus advantageously relates to the use of the peptide of the invention as a drug in the therapy of humans and animals. It also relates to the use of the peptide of the invention for the treatment of plants against microbial infections by applying the peptide directly on the plants. The invention thus relates to the use of a peptide or of a polypeptide of the invention as an antimicrobial agent and, more particularly, as an antibacterial agent active against gram-positive bacteria and against gram-negative bacteria. The invention also relates to the use of a peptide or a polypeptide of the invention for the preparation of an antimicrobial and, more particularly antibacterial composition for combating gram-positive and gram-negative bacteria.

The invention also relates to an antimicrobial composition comprising as an active agent the peptide of the invention or a polypeptide of the invention advantageously associated in the composition with an acceptable vehicle. The composition acts more particularly against gram-positive and gram-negative bacteria. The antimicrobial composition of the invention can also comprise another active principle such as another antimicrobial agent.

The term "vehicle" denotes any substance that is added to the peptide or to the polypeptide of the invention to favor their transport, avoid their substantial degradation in the composition and to preserve their antimicrobial properties. The vehicle is selected as a function of the type of application of the composition. In particular, when the composition is applied to a pharmaceutical usage for human and animal health, those skilled in the art will select the pharmaceutically acceptable vehicle adapted to the administration path of the pharmaceutical composition of the invention.

Thus, the pharmaceutical compositions according to the invention are constituted by at least the peptide or the polypeptide of the invention in free form or in the form of an addition salt with a pharmaceutically acceptable acid in the pure state or in the form of a composition in which it is associated with any other pharmaceutically compatible product. The pharmaceutical compositions according to the invention can be used orally, parenterally, rectally or topically.

Solid compositions that can be used for oral administration are tablets, pills, powders and the like in which the peptide or the polypeptide of the invention is mixed with one or several classically used inert diluting agents and possibly with other substances such as, e.g., a lubricant, colorant, coating agent and the like.

Liquid compositions that can be used for oral or ocular administration are suspensions, solutions, emulsions, pharmaceutically acceptable syrups containing classically used inert diluting agents and possibly other substances such as wetting products, sweeteners, thickeners and the like.

The sterile compositions for parenteral administration can be aqueous or non-aqueous solutions, suspensions or emulsions. Water, propylene glycol, vegetal oils or other suitable organic solvents can be used as solvent or vehicle. These compositions can also contain adjuvants such as softening agents, isotonizing agents, emulsifiers and the like.

The compositions for topical administration can be, e.g., creams, lotions, mouthwashes, nasal or ocular drops or aerosol.

When the antimicrobial composition of the invention is reserved for agrochemical use, the vehicle is an agrochemically acceptable vehicle adapted to being administered on plants or in the proximity of plants without degrading them.

In the antimicrobial compositions, the quantity of peptide or of polypeptide constituting subject matter of the invention that is advantageously used is between 0.1 and 50 µM as a function of the applications. However, it is evident that those skilled in the art know how to adapt this quantity as a function of the type of antimicrobial compositions, that is, pharmaceutical compositions or agrochemical compositions and as a function of the mode of administration of these compositions.

The invention also relates to a method for preventing and/or treating a microbial infection and, more particularly, a bacterial infection also caused by gram-positive and gram-negative bacteria. The method comprises administration to a subject of an efficacious quantity of a peptide, a polypeptide, a polynucleotide or a composition. The term "subject" denotes any animal or human for which a microbial infection has been diagnosed, but also any animal or human susceptible of suffering from this infection.

The following examples illustrate the invention and are not to be interpreted as limiting its scope. These examples refer more particularly to the demonstration of papillosin, its purification and its antibacterial activity.

I. Isolation of Papillosin

The biochemical characterization of this molecule is complete. Papillosin has been isolated from the circulating cells (hemocytes) of the sea squirt. It has been purified by high-performance liquid chromatography (HPLC) while following its activity with tests realized in vitro during the purification protocol.

I.1. Isolation from Hemocytes of Sea Squirts

Harvesting hemolymph is carried out after washing the sea squirts in ethanol (elimination of the mucilage) by section at the level of the foot. Separation of the two blood components (the plasma and the hemocytes) is made by centrifugation of the hemolymph (1000 g during 10 minutes). The hemocytes are obtained at the bottom in this manner.

The cellular bottom is homogenized in 10 volumes of 2 M acetic acid using a homogenizer, then, the homogenate is left 12 hours under agitation at 4° C. The homogenate is then centrifuged at 10000 g for 20 minutes at 4° C. The supenatant is then subjected to a first fractioning on an inverse-phase Sep-Pak cartridge (Sep-Pak Vac 12cc, Waters Corporation, USA, ref: WAT036915). The supernatant is deposited on the cartridge and three fractions of decreasing polarity are eluted by 3 solutions prepared from ultra-pure water (EUP) and acetonitrile (ACN, HPLC gradient grade, ACROS Organics, ref: 32573-0025) diluted with 0.05% trifluoroacetic acid (TFA, Fluka Chemika, ref: 91707):

10% ACN+90% EUP+0.05% TFA
60% ACN+40% EUP+0.05% TFA
80% ACN+20% BLIP 0.05% TFA

The hemocytic extracts are therefore separated into three fractions. These different fractions are then frozen at −80° C., lyophilized and placed in 1 ml EUP diluted with 0.05% TFA. A centrifugation is then performed (10000 g, 20 minutes at 4° C.). The supernatant constitutes the material that will be used for the HPLC.

I.2. Purification by HPLC

All the purification stages are carried out on an HPLC of the Waters type (model 1525 HPLC binary pump) equipped with a spectrophotometric detector (model 2487 dual λ absorbance detector, Waters), with an oven temperature-controlled with (thermostated) Peltier effect (model 560-CIL, Cluzeau info labo) and connected to a data acquisition system (Breeze software). The molecules eluted from the column are analyzed at the level of the UV detector with two wavelengths (224 and 280 nm).

The first HPLC stage is applied to the 60% Sep-Pak fraction containing the papillosin. The elution is carried out in inverse phase on a Sephasil C18 column (250*4.6 mm, Waters, ref: WAT054275) along a binary linear gradient: ACN and EUP diluted with 0.05% TFA. This gradient varies from 2% to 72% ACN over a time of 90 minutes, and the applied discharge is 1 ml/minute.

The eluted fractions are detected by displaying the absorbance peaks on the monitor and are collected in polyethylene tubes (low-binding Minisorp tubes, Merck eurolab, ref: 13183.01). These fractions will then be frozen, lyophilized and placed in EUP TFA 0.05%.

They are then tested for their antibacterial activities. The fraction containing the papillosin is subjected to a last purification stage carried out in inverse phase on a Sephasil C8 column (150*2.1 mm, Waters, ref: WAT056955). The elution gradient used frames the percentage of the elution of the fraction concerned during the preceding separation stage (29% ACN): the elution window is spread out/displayed on the percentages of acetonitrile from −5% to +5% relative to the percentage of elution previously obtained.

Furthermore, a spreading out of the gradient in time (10% in 40 minutes) is performed to obtain a finer separation. This second HPLC stage permits the obtention of the pure product. The elution is carried out in 40 minutes at a discharge of 0.3 ml/minute with a binary linear gradient: ACN/TFA and EUP/TFA.

II. Characterization of Papillosin

II.1. Tests of Antibacterial Activity During the Course of the Purification Stages The tests of antibacterial activity that allow the biological activity to be followed during the course of the purification stages are carried out in microplate (96 wells, Becton Dickinson, USA, ref: 18572). The various fractions harvested after the separation (Sep-Pak or HPLC) are frozen, lyophilized, then placed in EUP/TFA.

They are then placed at the rate of 10 µl into each well of the microplate and diluted with 100 µl bacterial culture (*E. coli*) in a poor broth environment (1% bactotryptone, 0.5% NaCl, pH 7.5) whose optical density (DO) is brought to 0.001. The entirety is placed under agitation (250 rpm) at 37° C. for 12 hours.

II.2. Biochemical Characterization of Papillosin

After purification, a combination of techniques of mass spectrometry and of Edman degradation permitted us to obtain the complete biochemical characterization of this peptide. It is a peptide with 34 amino acids with the following sequence:

GFWKKVGSAAWGGVKAAAKGAAVG-GLNALAKHIQ (SEQ ID No. 1). This peptide is a cationic molecule (estimated isoelectric point: 10.60) that is probably structured in an amphipathic helix α as suggested by the predictions of secondary structure.

II.3. Antibacterial Activity of Papillosin

Complementary tests were carried out to determine the spectrum of activity of papillosin. The minimal bactericidal concentration (MBC) for each bacterial strain tested is determined as follows: The peptide is placed in a solution containing 0.01% acetic acid and 0.2% bovine serum albumin (BSA), then, serial dilutions of 2 2 are realized in the same 0.01% solution of acetic acid and 0.2% BSA. 10 µl of each dilution are incubated in sterile 96-well plates (Becton Dickinson, USA, ref: 18572) in the presence of 100 µl of a bacterial suspension brought to an optical density of 0.001 at 600 nm in the Mueller Hinton environment (MLHB, SIGMA, ref: M-9677).

The bacterial growth is monitored after 18 hours of incubation under agitation. The MBC is determined by spreading out the content of the first three wells in which no bacterial growth was observed. This spreading out was carried out on Petri dishes on which an agar was poured prepared from the Mueller Hinton environment. These dishes were then incubated 18 hours. The MBC corresponds to the lowest concentration of peptide for which no bacterial colony was observed on the incubated dishes.

Table 1 shows the spectrum of activity of the molecule. In sum, papillosin has a powerful bacteriolytic activity on gram-positive and gram-negative bacteria.

TABLE 1

| Spectrum of activity of papillosin (MBC values expressed in µM) | |
|---|---|
| Bacteria | MBC |
| gram-positive bacteria | |
| *M. luteus* | 0.125-0.25 |
| *S. aureus* | 0.5-1 |
| gram-negative bacteria | |
| *E. coli* | 0.25-0.5 |

The invention claimed is:

1. An isolated peptide consisting of the amino acid sequence GFWKKVGSAAWGGVKAAAKGAAVG-GLNALAKHIQ (SEQ ID NO: 1).

2. An isolated polynucleotide that encodes the peptide of claim 1.

3. A cloning and/or expression vector that contains the polynucleotide in accordance with claim 2.

4. The vector according to claim 3, further comprising at least one element selected from the group consisting of promoters, inducible promoters and terminator elements.

5. The vector according to claim 3, further-comprising elements that permit maintenance and-replication in a host organism.

6. An antimicrobial composition comprising the peptide according to claim 1, as an active agent and a pharmaceutically acceptable vehicle.

7. An antimicrobial composition comprising the peptide according to claim 1 as an active agent and an agrochemically acceptable vehicle.

8. A method of treating a microbial infection comprising administering a therapeutically effective amount of the composition according to claim 6.

9. The method according to claim 8 wherein the bacterial infection is caused by gram-positive and/or gram-negative bacteria.

10. The antimicrobial composition according to claim 6, containing between 0.1 and 50 μM of the peptide.

11. The antimicrobial composition according to claim 7, containing between 0.1 and 50 μM of the peptide.

12. A method of a inhibiting microbial growth comprising providing an effective amount of the isolated peptide of claim 1 or the composition of claim 6.

13. The method according to claim 12, wherein the inhibition of microbial growth inhibits the growth of gram-positive and/or gram-negative bacteria.

* * * * *